United States Patent [19]

Leitereg et al.

[11] 3,962,339

[45] June 8, 1976

[54] PROCESS FOR THE PRODUCTION OF BICYCLO DECENONE DERIVATIVES

[75] Inventors: Theodore J. Leitereg, Albany; Dante G. Guadagni, Moraga; Roy Teranishi, Berkeley, all of Calif.

[73] Assignee: The United States of America as represented by the Secretary of Agriculture, Washington, D.C.

[22] Filed: Apr. 6, 1973

[21] Appl. No.: 348,556

Related U.S. Application Data

[62] Division of Ser. No. 113,678, Feb. 8, 1971, abandoned.

[52] U.S. Cl. .......... 260/586 C; 252/522; 260/586 F

[51] Int. Cl.[2] .......... C07C 45/00

[58] Field of Search .......... 260/586 R, 587, 586 C

[56] References Cited

UNITED STATES PATENTS

| | | | |
|---|---|---|---|
| 2,671,808 | 3/1954 | Johnston et al. | 260/586 R |
| 3,538,164 | 11/1970 | Leffingwell | 260/587 |
| 3,560,571 | 2/1971 | Kropp | 260/587 |

OTHER PUBLICATIONS

MacLeod, "C.A.," vol. 64, p. 12730b (1966).

Erdtman, et al., "C.A.," vol. 59, p. 1691a (1963).

*Primary Examiner*—Norman Morgenstern
*Attorney, Agent, or Firm*—M. Howard Silverstein; William Takacs

[57] ABSTRACT

Limonene is epoxidized and the product reacted with $BF_3$-etherate to produce dihydrocarvone which is condensed with 3-peten-2-one to give a mixture of the 5,6-dimethyl-9-isopropenyl and 5,10-dimethyl-7-isopropenyl derivatives of bicyclo [4,4,0] dec-1-en-3-one. The mixture is useful as an odorant to provide a woody aroma in soaps, cosmetics, toiletries, etc. Individual isomers may be separated from the mixture by such techniques as preparative glc.

1 Claim, No Drawings

PROCESS FOR THE PRODUCTION OF BICYCLO DECENONE DERIVATIVES

This is a division of our co-pending application Ser. No. 113,678, filed Feb. 8, 1971, now abandoned.

A non-exclusive, irrevocable, royalty-free license in the invention herein described, throughout the world for all purposes of the United States Government, with the power to grant sublicenses for such purposes, is hereby granted to the Government of the United States of America.

DESCRIPTION OF THE INVENTION

This invention relates to and has among its objects the provision of new bicyclo [4,4,0] dec-1-en-3-one derivatives, that is, compounds which contain the following nucleus:

Formula I

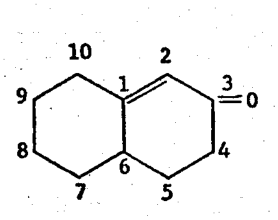

The products of the invention are especially useful as odorants for soaps, perfumes and cosmetics in general. The objects of the invention also include methods for preparing and utilizing these compounds. Further objects of the invention will be evident from the following description wherein parts and percentages are by weight unless otherwise specified. Temperatures are given in °C.

In the perfume industry "woody" aromas such as cedar, sandalwood, pine, etc. are very desirable, but compounds which exhibit these aromas are expensive. An inexpensive and easy method for the production of materials which have similar aromas is, therefore, quite useful. A primary object of the invention is the provision of methods and compounds which achieve this goal.

One aspect of the invention concerns the provision of a novel composition of matter (hereinafter designated as DIDO), being a mixture of 5,6-dimethyl-9-isopropenyl-bicyclo [4,4,0] dec-1-en-3-one and 5,10-dimethyl-7-isopropenyl-bicyclo [4,4,0] dec-1-en-3-one, these having the structures shown in Formulas II and III below and designated hereinafter as 9-DIDO and 7-DIDO, respectively.

Formula II (9-DIDO)

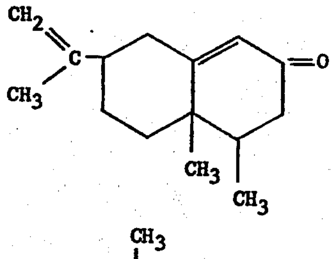

Formula III (7-DIDO)

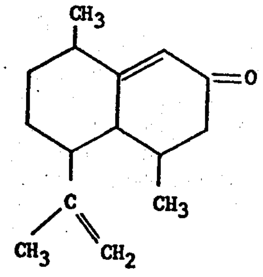

Referring to Formulas II and III, each of the methyl and isopropenyl substituents may be in either $\alpha$ or $\beta$ configuration. Ordinarily, the composition of the invention (DIDO) will contain a mixture of individual stereoisomers wherein these substituents will be in different geometric configurations.

The composition of the invention (DIDO) exhibits an intense woody aroma and is useful for imparting such aroma to soaps, detergents, shaving lotions, hair dressings, perfumes, toilet waters, colognes, deodorants, deodorizers, and the like. Such products are herein referred to generically as cosmetics and toilet preparations.

A factor which makes the products of the invention particularly useful as odorants in their stability. For example, they are not decomposed by contact with alkaline materials. As a result, they can be used in soaps and other preparations of an alkaline nature. This is in sharp contrast to many odorants--particularly those containing ester linkages--which will undergo hydrolysis when contacted with soaps, detergents, or other preparations of an alkaline nature. Another advantage of the products of the invention is that they are stable in air. They do not undergo oxidation even afer prolonged contact with air.

Another aspect of the invention concerns the method of synthesizing DIDO. This involves starting with limonene in any of its optical forms. A preferred form is (+)-limonene, an inexpensive compound which comprises about 95 percent of orange oil. It is precisely the availability of (+)-limonene in almost pure form, 50 million pounds per year as waste material, which makes the invention advantageous. However, (−)-limonene or any mixtures of (+)- and (−)-limonene will produce essentially the same isomeric mixtures useful for the same purposes as above described. Since (+)- and (−)-limonene differ only as far as optical properties are concerned, they are chemically equivalent and, therefore, interchangeable in the synthesis.

In a first step of the synthesis of the invention, limonene is epoxidized to form limonene monoxide. This is readily accomplished by reacting limonene with m-chloroperbenzoic acid or other peroxy compound such as hydrogen peroxide, peracetic acid, perbenzoic acid, t-butyl peroxide, or the like.

In a second step, the limonene monoxide is treated to open the epoxide ring and form dihydrocarvone. This is readily accomplished by reacting limonene monoxide with boron trifluoride-etherate, using dimethylsulfoxide as the solvent. The use of this solvent is a critical feature of the reaction; other solvents give rise to a variety of undesirable by-products. It should be understood that in the conversion of limonene to dihydrocarvone, it is not necessary to isolate the intermediate limonene monoxide in a pure state. Since dihydrocarvone is easily separable from the starting materials, a simple distillation at this stage (after conducting the epoxide ring opening) yields dihydrocarvone in an essentially pure form.

In a third step of the synthesis, dihydrocarvone is condensed with 3-penten-2-one in the presence of a base, for example, sodium hydride, an alkali metal alcoholate such as potassium t-amylate, pyrrolidine, or the like. The condensation is generally carried out under reflux (about 60°–120° C.) in a solvent such as benzene, toluene, tetrahydrofuran, t-amyl alcohol, or the like. This condensation produces the desired DIDO mixture. However, the product at this point usually contains some by-product hydroxy derivatives, notably Formula IV 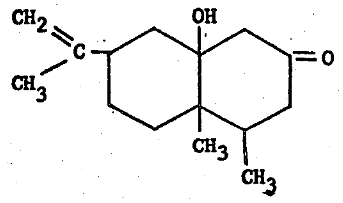

These hydroxy derivatives have no odor and are easily dehydrated to the corresponding unsaturated derivatives, for example, the hydroxy compound of Formula IV being dehydrated to form 9-DIDO. The dehydration is accomplished by treating the crude DIDO preparation with a base such as potassium t-butoxide in dimethylsulfoxide at about room temperature. Conventional purification steps such as extraction and distillation under reduced pressure are then applied to yield the desired DIDO mixture free from unreacted dihydrocarvone.

The synthesis of the invention is illustrated by the following formulas:

limonene is used as the starting material except that in this case, the individual compounds will all contain the isopropenyl substituent in α configuration. Where the starting material is racemic limonene or other mixture of the (+) and (−) forms, the DIDO mixture will contain a large number of individuals differing as to the geometric configuration of the isopropenyl substituents as well as the methyl substituents. It is thus obvious that choice of the form of limonene used as the starting material offers a certain ability to control the composition of the products of the invention. Another plan along these lines involves selection of the base and solvent used in the step of condensing dihydrocarvone with 3-penten-2-one. As shown in Example 6 below, the use of sodium hydride in conjunction with tetrahydrofuran or potassium t-amylate in conjunction with t-amyl alcohol yields a DIDO product which contains chiefly stereoisomeric forms of 9-DIDO, whereas when pyrrolidine is used as the base with toluene as the solvent, the product is chiefly the stereoisomers of 7-DIDO.

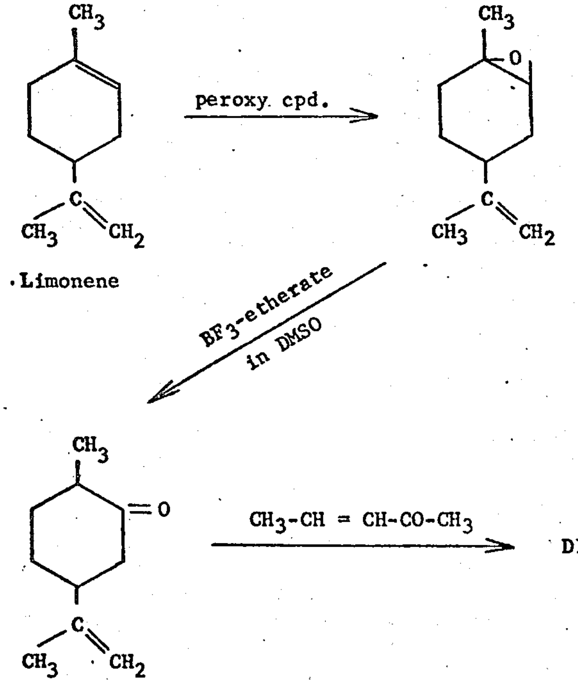

Limonene monoxide

Limonene

Dihydrocarvone

DIDO mixture

The DIDO mixture, as explained above, is useful in such form as an odorant. It is within the compass of the invention, moreover, to fractionate the mixture into its 9-DIDO and 7-DIDO components or even to apply a higher degree of fractionation to isolate individual stereoisomers of either the 9- or 7-isomers. Also, individual compounds or fractions may be re-combined to produce an aroma which is desired for a particular application. For the fractionations one may use such known techniques as fractional distillation, preparative glc, or column chromatography.

It may be observed that when (+)-limonene is used as the starting material, the individual compounds forming the DIDO mixture will all contain the isopropenyl substituent in β configuration; the geometric variation will be restricted to the configuration of the methyl groups. A parallel situation is presented when (−)-

EXAMPLES

The invention is further demonstrated by the following illustrative examples.

EXAMPLE 1

Synthesis of (+)-Limonene Monoxide

A 500-ml, 3-necked, round-bottomed flask was flushed with dry nitrogen after being fitted with a nitrogen inlet tube and a 250-ml pressure-equalizing dropping funnel. Then, 8.0 g. of (+)-limonene from orange oil was dissolved in 50 ml. of methylene chloride and placed in the flask. The solution was stirred with a magnetic stirrer and maintained at 20° with a water bath. In the funnel were placed 10.0 g. of m-chloroperbenzoic acid and 140 ml. of methylene chloride. This solution was added dropwise to the stirring (+)-limonene solution over a 45-minute period and under a positive pressure of dry nitrogen. When the addition was completed, the pressure-equalizing dropping funnel was removed and a calcium chloride drying tube was inserted in its place. The nitrogen flow was stopped, and the contents of the flask were stirred for 16 hours.

To the flask was added 100 ml. of 10 percent sodium sulfite and stirring was continued an additional 15 minutes. Finally, 100 ml. of saturated sodium bicarbonate was added and the contents were transferred to a one-liter separatory funnel. The layers were separated and the aqueous layer was extracted twice with 50 ml. of ether. The organic layers were combined, dried, and evaporated to give 8.69 g. of crude material. Glc analysis indicated approximately 70 percent of the (+)-limonene monoxide (cis and trans formed in a ratio of 1:1), 5 percent of (+)-limonene dioxide, and 25 percent of unreacted (+)-limonene. The (+)-limonene monoxide was distilled on a Teflon spinning band apparatus to a purity of 99 percent by glc.

EXAMPLE 2

Synthesis of (+)-Dihydrocarvone

To a solution of 25.3 g. of (+)-limonene monoxide in 30 ml. of dry dimethylsulfoxide was added 1 ml. of distilled boron trifluoride-etherate. The solution was stirred magnetically for 22 hours at 65°.

After cooling, the contents were poured onto 100 ml. of ice-water and stirred for 15 minutes. The contents were transferred to a separatory funnel with 100 ml. of ether. The layers were separated and the aqueous layer was extracted twice with two 75-ml. portions of ether. The ether layers were combined, washed three times with 100-ml. portions of water, once with 100 ml. of brine, dried, and evaporated to give 26.7 g. of crude material which was approximately 70% (+)-dihydrocarvone by glc. This material was distilled on a Teflon spinning band column to give 15.6 g. of approximately 99 percent pure (+)-dihydrocarvone (mixture of diastereomers), whose spectral properties were identical to those reported in the literature.

EXAMPLE 3

Synthesis of DIDO Mixture

A. A 100-ml., 3-necked, round-bottomed flask fitted with a gas-inlet tube, a dropping funnel, and a magnetic stirrer was flushed with dry nitrogen. Under a positive pressure of nitrogen 3.9 g. of a sodium hydride mineral oil dispersion was added to the flask which contained 30 ml. of dry tetrahydrofuran. Then, 5 g. of (+)-dihydrocarvone in 15 ml. of dry tetrahydrofuran was added dropwise by means of a funnel. After a few drops of the (+)-dihydrocarvone was added, two drops of ethanol was introduced to aid the start of the reaction of converting the dihydrocarvone into its anionic form. Then the remaining (+)-dihydrocarvone solution was added and the mixture was stirred at reflux for 2 hours.

After cooling, 2.9 g. of 3-penten-2-one in 15 ml. of tetrahydrofuran was added and the mixture was refluxed for 16 hours and was allowed to come to room temperature. Thirty ml. of water was added and the contents transferred to a separatory funnel with 50 ml. of ether. The layers were separated and the aqueous layer was extracted twice with 50-ml. portions of ether. The ether layers were combined, washed twice with 50-ml. portions of water, once with 50 ml. of brine, dried, and evaporated.

B. The crude material was dissolved in 30 ml. of dimethylsulfoxide and stirred with 1 g. of potassium tert-butoxide for 1.5 hours to dehydrate the alcohols formed as by-products. The mixture was quickly transferred to a flask containing 50 ml. of ice-water. After stirring for 15 minutes, 50 ml. of ether was added and the contents placed in a separatory funnel. The layers were separated and the aqueous layer washed twice with two 50-ml. portions of ether. The ether layers were washed three times with 50-ml. portions of water, once with 50 ml. of brine, dried, and evaporated to give 7.7 g. of crude material. This material was distilled at 0.003 mm Hg to give 2.3 g. of unreacted (+)-dihydrocarvone (b.p. 27–40) and 3.8 g. of material (b.p. 85–115) whose infrared (IR) spectrum showed bands at 1675 (broad) and 1893 $cm^{-1}$. Glc analysis, along with mass spectral, nmr, UV, ORD, and X-ray crystallographic analysis, indicated that this material was a mixture of stereoisomers of 9-DIDO (88%) and of 7-DIDO (12%). Application of glc indicated the presence of four individual stereoisomers of 9-DIDO and four of 7-DIDO, each having a molecular weight of 218 as determined by mass spectroscopy. The proportions of the eight individuals are given in the following table.

| | Individual | | Proportion, % |
|---|---|---|---|
| a. | Stereoisomer of | 9-DIDO | 2 |
| b. | " | 9-DIDO | 16 |
| c. | " | 9-DIDO | 9 |
| d. | " | 9-DIDO | 61 |
| e. | " | 7-DIDO | 4 |
| f. | " | 7-DIDO | 6 |
| g. | " | 7-DIDO | 1 |
| h. | " | 7-DIDO | 1 |

The individual designated as d was isolated and characterized as shown in Example 4 below.

EXAMPLE 4

Several of the above individuals referred to in the table above were separated in a pure state from the DIDO mixture. This was accomplished by preparative glc on a 12 ft. by 0.5 in. stainless steel column packed with 1 percent Carbowax 20 M at a temperature of 175° C. and a helium pressure of 40 psig. The nmr values of these individuals was as follows:

Individual d (stereoisomer of 9-DIDO, 61 percent of mixture): doublet at 0.96–0.89 ppm (3H), singlet at 1.09 (3H), singlet (slightly split) at 1.69 (3H), doublet at 4.83–4.75 (2H), and a singlet (slightly split) at 5.68 (1H).

Individual e (stereoisomer of 7-DIDO, 4 percent of mixture): doublet at 1.02–0.96 (3H), doublet at 1.23–1.17 (3H), triplet (J=1) at 1.70 (3H), doublet (J=1) at 4.75–4.76 (2H), and a singlet at 5.68 (1H).

Individual f (stereoisomer of 7-DIDO, 6 percent of mixture): doublet at 1.04–0.98 (3H), doublet at 1.14–1.08 (3H), triplet (J=1) at 1.68 (3H), doublet (J=1) at 1.68 (3H), doublet (J=1) at 4.76–4.77 (2H), and a singlet at 5.61 (1H).

Individual d, the major component of the DIDO mixture, was determined to be 5-α-6-α-dimethyl-9-β-isopropenyl-bicyclo [4,4,0] dec-1-en-3-one.

EXAMPLE 5 - Aroma Evaluation

The DIDO mixture and several individual stereoisomers separated from the mixture by preparative glc were subjected to aroma evaluation, using a trained panel of 20 judges. In this evaluation, the materials were progressively diluted with increasing quantities of water to determine the odor threshold of each, the values found being given in the table below.

It was also found that each of the materials had an aroma best described as woody.

To provide a point of reference, the known compound (+)-nootkatone

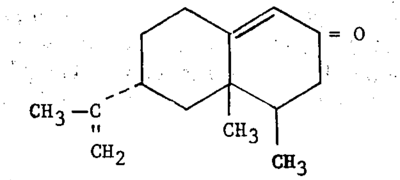

was also evaluated for odor threshold. It may be noted that this compound is the flavor principle of grapefruit and exhibits an intense aroma characteristic of that fruit.

| Compound | Odor threshold, parts per million |
|---|---|
| DIDO Mixture | 8 |
| b. Stereoisomer* of 9-DIDO (16% of DIDO mixture) | 1.8 |
| d. Stereoisomer of 9-DIDO (61% of DIDO mixture) | 20 |
| e. Stereoisomer of 7-DIDO (4% of DIDO mixture) | 0.8 |
| f. Stereoisomer of 7-DIDO (6% of DIDO mixture) | 1.5 |
| (+)-Nootkatone | 0.2 |

*Purity of this material was ca. 75%.

EXAMPLE 6

Dihydrocarvone was condensed with 3-penten-2-one as described in Example 3, except for changes in the base and solvent used in the condensation reaction (part A of Example 3). In one run, potassium t-amylate was used as the base and t-amyl alcohol as the solvent. In another run, pyrrolidine (base) was used in conjunction with toluene (solvent). The products were worked up and the proportion of different stereoisomers in each product determined as in Example 3. The results are reported below, those of Example 3 being included for purpose of comparison

| Base | Solvent | Yield of DIDO mixture, % | Yield of isomers, % 9-DIDO a | b | c | d | e | 7-DIDO f | g | h |
|---|---|---|---|---|---|---|---|---|---|---|
| Sod. hydride | tetrahydrofuran | 53 | 2 | 16 | 9 | 61 | 4 | 6 | 1 | 1 |
| Pot. t-amylate | t-amyl alc. | 48* | 1 | 35 | 5 | 47 | 2 | 4 | 0 | 0 |
| Pyrrolidine | toluene | 38 | 1 | 2 | 1 | 4 | 28 | 58 | 4 | 2 |

*6% of a compound of undetermined structure was also formed in this reaction.

It is particularly to be noted that in the first two runs, the products were primarily mixtures of the stereoisomers of 9-DIDO, whereas in the third run the product was primarily a mixture of stereoisomers of 7-DIDO.

Having thus described our invention, we claim:

1. A method for preparing a mixture of the compounds

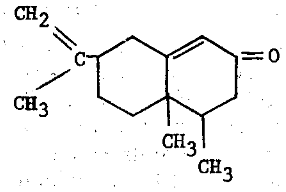

and

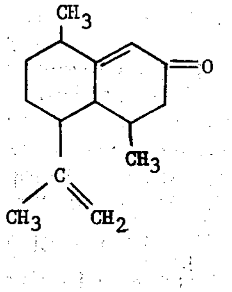

and including stereoisomers of each of these compounds, which comprises a. condensing dihydrocarvone with 3-penten-2-one in the presence of sodium hydride at a temperature of about 60°–120° C., and b. treating the resulting condensation product with potassium tert-butoxide in dimethylsulphoxide at room temperature.

* * * * *